United States Patent [19]

Maarschalkerweerd

[11] Patent Number: 5,006,244

[45] Date of Patent: * Apr. 9, 1991

[54] FLUID PURIFICATION DEVICE

[75] Inventor: Jan Maarschalkerweerd, Lambeth, Canada

[73] Assignee: Trojan Technologies, Inc., London, Canada

[*] Notice: The portion of the term of this patent subsequent to Oct. 10, 2006 has been disclaimed.

[21] Appl. No.: 359,647

[22] Filed: May 31, 1989

Related U.S. Application Data

[62] Division of Ser. No. 243,845, Sep. 13, 1988, Pat. No. 4,872,980.

[51] Int. Cl.$^5$ ................................................ C02F 1/32
[52] U.S. Cl. ................................ 210/243; 210/192; 250/432 R; 250/436; 422/24; 362/101
[58] Field of Search ....................... 210/243, 192, 748; 250/435, 436, 432; 422/24; 362/101, 221, 230, 263, 391

[56] References Cited

U.S. PATENT DOCUMENTS

| | | | |
|---|---|---|---|
| 3,462,597 | 8/1969 | Young | 422/2 |
| 3,948,772 | 4/1976 | Ellner | 422/2 |
| 4,255,663 | 3/1981 | Lewis | 250/436 |
| 4,296,328 | 10/1981 | Regan | 250/436 |
| 4,367,410 | 1/1983 | Wood | 250/436 |
| 4,400,270 | 8/1983 | Hillman | 250/436 |
| 4,482,809 | 11/1984 | Maarschalkerweerd | 250/436 |
| 4,755,292 | 7/1988 | Merriam | 210/192 |
| 4,757,205 | 7/1988 | Latel et al. | 250/435 |
| 4,873,980 | 10/1989 | Maarschalkerweerd | 210/243 |

Primary Examiner—Robert A. Dawson
Assistant Examiner—Matthew O. Savage
Attorney, Agent, or Firm—William E. Mouzavires

[57] ABSTRACT

A fluid purification device including an inverted U-shape frame whose legs support a plurality of lamp assemblies each including an ultraviolet lamp received in a protective sleeve. One of the legs is hollow and receives lead wires connected to the lamps through openings spaced along the leg. The protective sleeves at one of their ends are resiliently mounted to the hollow leg at the openings, and seals are provided to prevent fluid from entering into the hollow leg and the protective sleeve. The other ends of the protective sleeves are closed and held in receptacles in the other frame leg which is formed by two plates fixed to each other. "O" rings provided along the other leg receive the protective sleeves to provide flexible seats. An electrical ballast controlling voltage and amperage at the lamps is incorporated in the frame.

16 Claims, 2 Drawing Sheets

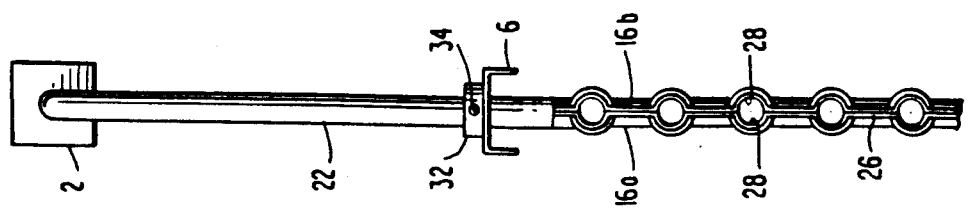
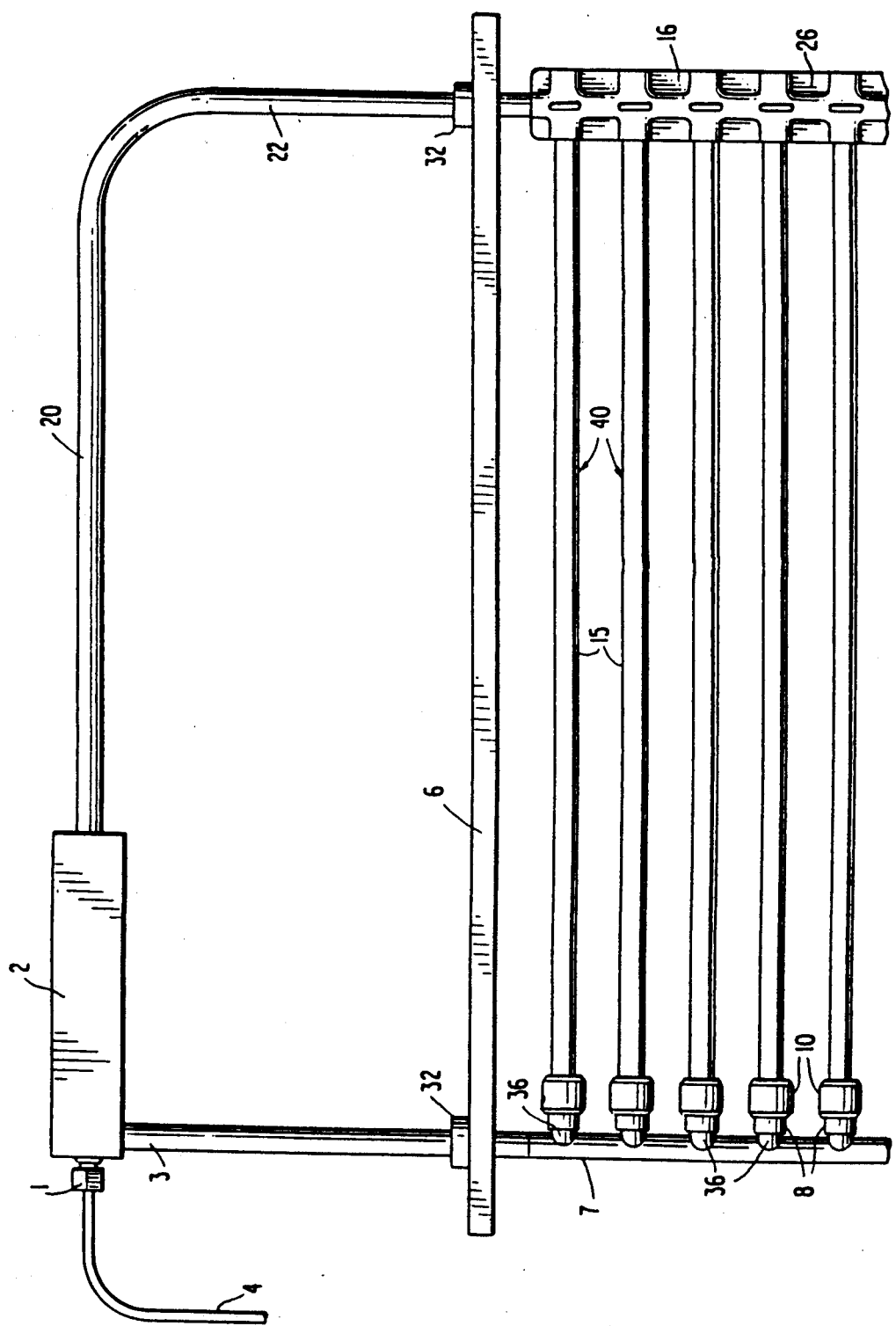

FLUID PURIFICATION DEVICE

RELATED APPLICATION

This application is a division of my prior co-pending patent application Ser. No. 07/243,845 filed Sept. 13, 1988 and issued into U.S. Pat. No. 4,872,980 on Oct. 10, 1989.

BACKGROUND OF THE INVENTION

The present invention relates to purification or sterilization of fluids, such as waste water, through ultraviolet light rays which are capable of killing or destroying unwanted microorganisms in fluids as is well-known. More specifically, the present invention relates to ultraviolet lamp systems which are immersed in the fluid to be purified. The systems may include a plurality of lamp modules each containing a plurality of lamp assemblies supported in parallel by and between spaced vertical legs forming a part of the module frame such as, for example, disclosed in U.S. Pat. No. 4,482,809 assigned by the inventor herein to the same assignee of the subject application. In the module device of this patent, the ultraviolet lamps are mounted to the legs of the frame by their surrounding protective sleeves whose opposite ends are open and mounted and sealed in sockets spaced along the legs. The lamps are powered through lead wires extending from an external control panel and received in both legs of the frame which are hollow for this purpose. The lead wires are connected to opposite ends of the lamps through contacts in the sockets; there being a separate pair of lead wires connected to each lamp at the opposite ends thereof respectively. The voltage and amperage of the lamps are controlled at a control panel located externally of the lamp modules.

OBJECTS OF THE PRESENT INVENTION

An object of the present invention is to provide certain improvements in fluid purification devices of the type shown, for example, in U.S. Pat. No. 4,482,809 mentioned above. Included herein is the provision of a fluid purification device of the type described which simplifies and improves the mounting and sealing of the lamp assemblies while simplifying and reducing the electrical connections for the lamps. Additionally included is the provision of such a device having an improved frame which is more economical to manufacture and facilitates assembly of the lamp units. Another object is to provide such a fluid purification device incorporating in its own frame, an electrical ballast for controlling the voltage and amperage through the lamps.

SUMMARY OF INVENTION

A preferred embodiment of the device of the present invention includes a frame having spaced legs in which a plurality of lamp assemblies are mounted; each assembly including an elongated ultraviolet lamp and a surrounding protective sleeve closed at one end. One of the legs has a hollow passage receiving lead wires for powering all of the lamps. The lead wires are connected to one of the ends of the lamps through openings spaced along the hollow leg. One of the ends of the protective sleeves is open and mounted in an improved manner to the hollow legs in alignment with the leg openings which are sealed by closures containing electrical conductors interconnecting the lead wires and the lamps. The inner and outer surfaces of the protective sleeves at said one end thereof are sealed to prevent fluid contact with the electrical connections.

The other ends of the protective sleeves are closed and mounted in resilient seats carried in receptacles formed in the other frame leg. The latter is formed by two plates fixed together with registering recesses forming the receptacles. An electrical ballast for controlling the voltage and amperage at the lamps is incorporated in the frame of the device.

DRAWINGS

Other objects and advantages of the present invention will become apparent from the following more detailed description taken in conjunction with the attached drawings in which:

FIG. 1 is a side elevational view of a water purifying device constituting a preferred embodiment of the present invention;

FIG. 4 is an end elevational view of the device.

DETAILED DESCRIPTION

Figure 2:
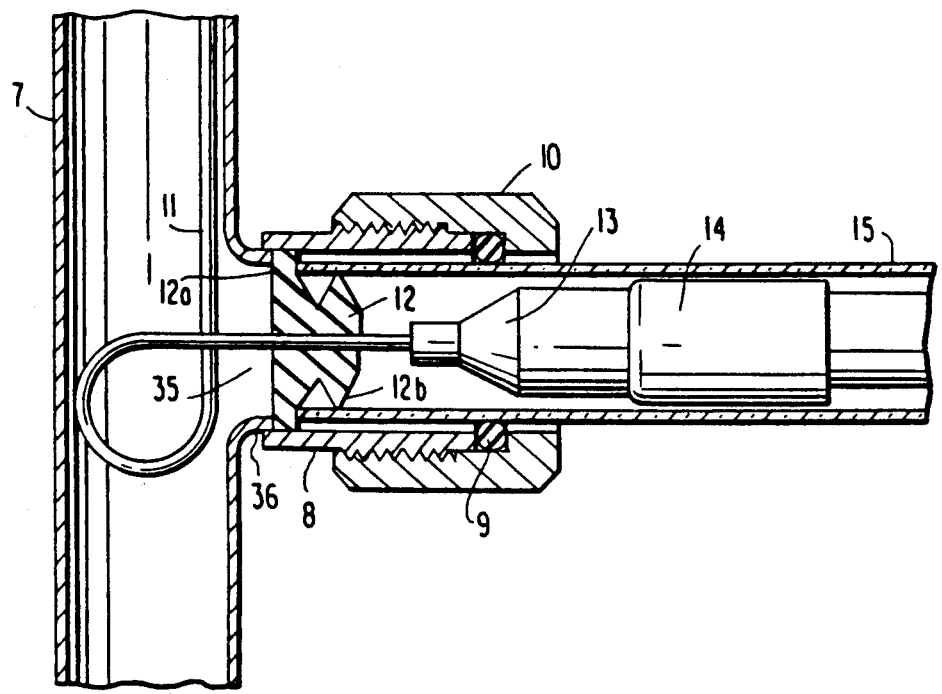
FIG. 2 is an enlarged, fragmental, cross-sectional view of an end portion of the device where a lamp assembly is mounted in the frame of the device.

Referring to the drawings in detail there is shown for illustrative purposes only, a fluid purification device constituting a preferred embodiment of the invention. The device is a module to be used with other similar or identical modules for purifying fluids such as waste water with ultraviolet rays according to purification principles which are well-known and need not be described here. Referring to FIG. 1, the device in its preferred form, includes an inverted U-shape frame including opposite legs interconnected at the top by a cross piece 20 which includes a ballast 2 connected to a power cord 4 by a strain relief 1. Ballast 2 controls the voltage and amperage through ultraviolet lamps 14 mounted to and between the frame legs as will be described below. To initially energize the lamps 14, high voltage on the order of 600 volts at the ballast is required but once the lamps are energized, a lower voltage, for example, 180 volts at the ballast is sufficient and this variation of the voltage is provided by the ballast. Ballast 2 also functions to limit the amperage through the lamps.

The frame leg on the left as shown in FIG. 1 includes upper and lower hollow tubular sections 3 and 7 joined, such as by butt welding, to each other in axial alignment, with the lower end of section 7 being closed. The frame leg shown on the right in FIG. 1 is also formed in two joined sections including an upper section 22 which may be integral with cross piece 20 and a lower section 16 formed by two plates 16a and 16b. The latter are welded together at flat web portions 26 and are formed with registering semi-cylindrical recesses 28 providing cylindrical receptacles 30 extending transversely between the webs for receiving the lamp assemblies as will be described below. Mounted to and between intermediate portions of the frame legs is an inverted generally U-shaped channel 6 having collars 32 fixed thereto with set screws 34 for securing channel 6 in desired position. Channel 6 serves to reinforce the frame and also as a barrier to the ultraviolet light.

Lower leg section 7 has a plurality of openings 35 formed along its length at spaced locations. The lamp assemblies are mounted at one of their ends to leg 7 in alignment with openings 35 respectively. In the preferred embodiment, cylindrical mounting flanges or flares 36 are fixed to or formed with the leg section 7 about the openings 35, and fixed about each of the mounting flanges 36, such as by welding, is a cylindrical mounting sleeve 8. The lamp assemblies, generally designated 40 in FIG. 1, are mounted at their opposite ends in mounting sleeves 8 and receptacles 30 respectively.

Figure 3:
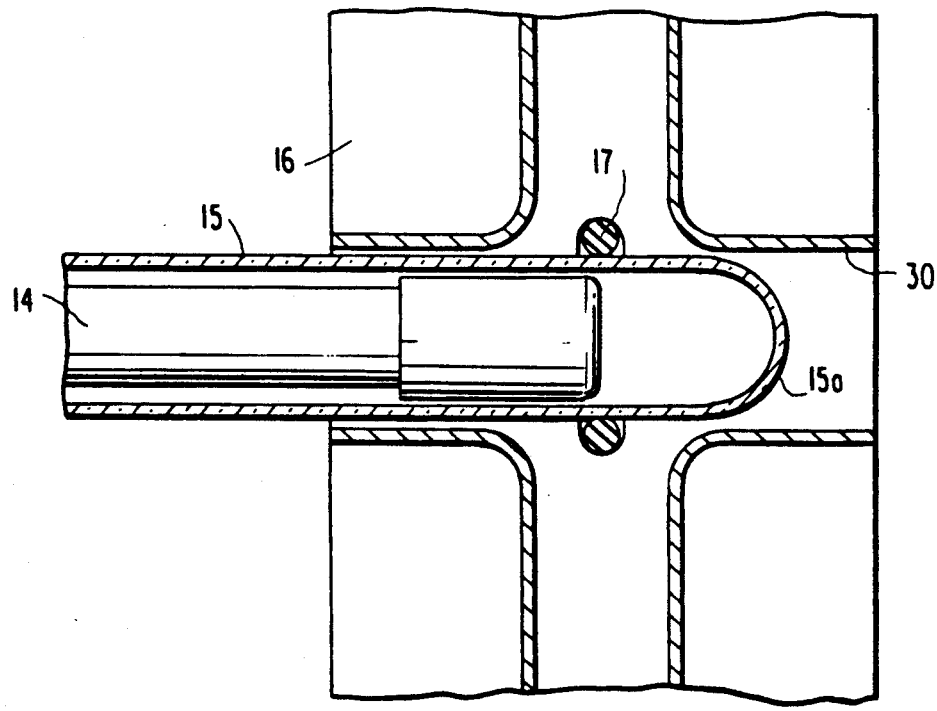
FIG. 3 is a view generally similar to FIG. 2 but taken at an opposite end portion of the device.

Each lamp assembly 40 includes an elongated ultraviolet lamp 14 and an elongated protective quartz sleeve 15 surrounding the lamp 14 to fully enclose the same. In the preferred embodiment, the right end of the protective sleeve 15, as shown in FIG. 1, extends beyond the adjacent end of lamp 14 and is closed at 15a (see FIG. 3). The left end of protective sleeve 15 extends beyond the adjacent end of lamp 14 and is formed with an opening in alignment with the opening 35. The left end of the protective sleeve 15 is mounted coaxially within the mounting sleeve 8 while the right end is mounted in receptacle 30 as best shown in FIG. 3. In order to prevent breakage of the protective sleeve at its right end portion, a plurality of flexible and resilient seats, preferably "0" rings 17 are provided in the split leg section to surround the receptacles 30 and receive the protective sleeves respectively as shown in FIG. 3.

In the preferred embodiment shown, each lamp 14 has, on the left end thereof as shown, a connector 13 having contact pins (not shown) received in sockets formed in the end of the lamp. Lead wires 11 provided for driving the lamps respectively extend from the connectors 13 through openings 35 and vertically within the hollow passages of leg sections 3 and 7. All of the lead wires 11 for driving all of the lamps 14 of each module are located in the left-hand leg sections 3 and 7 from which they are connected to the ballast 2.

In order to seal the space between the mounting sleeve 8 and the protective sleeve 15, an annular seal, preferably an "0" ring 9, is mounted about each protective sleeve 15 at the end of the mounting sleeve 8. A nut 10 is threaded onto mounting sleeve 8 and has an internal shoulder engaged with the "0" ring 9. Advancement of nut 10 along mounting sleeve 8 will deform the "0" ring radially inwardly to establish a fluid tight seal about the protective sleeve 8. "0" rings 9 also help to provide a resilient mount for the lamp assemblies.

In order to prevent entry of fluid through openings 35 and into the hollow leg section 7, each of the openings 35 is sealed closed by a closure or plug 12 made of a suitable flexible rubberlike material. In the preferred embodiment shown in FIG. 2, closure 12 includes a first sealing segment 12a having a generally cylindrical shape and butted against the flanges 36 surrounding openings 35 with the peripheral surface of the sealing segment 12a continuously in sealing engagement with the inside surface of the mounting sleeve 8 as shown in FIG. 2. For added insurance, closure 12 is formed with another sealing segment 12b axially spaced inwardly of segment 12a and formed by opposed frusto-conical portions defining a thin circular sealing lip in continuous sealing engagement with the inside surface of the protective sleeve 15; it being understood that the diameter of sealing segment 12b is less than that of segment 12a. Closure 12 also provides a flexible and resilient cushion mount for the end of the protective sleeve 15 which abuts against the sealing segment 12a while being received on sealing segment 12b as shown in FIG. 2. It will thus be seen that should the protective sleeve 15 break allowing fluid to pass "0" ring 9, the fluid will be prevented from passing sealing segments 12a or 12b to enter the leg 7.

In the preferred embodiment shown, the closures 12 are molded about a respective lead wire 11 which extends inwardly from the closure 12 to the connector 13. However, in other embodiments not shown, the connector 13 may be formed or located within the closure 12 itself which may be an electrical receptacle. Additionally, other types of electrical connections to the lamps 14 may be made at or in the closure 12.

The various parts of the module frame including split leg sections 16a, 16b may be made from suitable non-corrosive material such as stainless steel. Also, if desired, nuts 10 may be made from plastic such as DELRIN material.

It will be understood that although only one module has been shown and described, in use a typical installation at a fluid purification site, will include a plurality of modules arranged such as shown in U.S. Pat. No. 4,482,809, reference to which is hereby made for disclosure purposes.

It will thus be seen that the present invention reduces the number of external lead wires required for the lamps while also placing them in a single frame leg thus allowing the other leg to be economically made and without electrical connections and seals at that leg. In addition, the incorporation of the ballast in the frame itself obviates the need of an external control panel to further reduce parts and cost. Moreover, the present invention improves the mounting and sealing of the lamp assemblies while, at the same time, preventing fluid contact with the lead wires and electrical connections.

What is claimed is:

1. A fluid purification module adapted to be inserted in a body of water to be purified, the module comprising in combination a frame including a pair of opposed legs laterally spaced from each other and adapted for insertion into the water to be purified, a plurality of water purification lamps extending between and supported by said legs, each lamp having one end thereof located towards said one leg and an opposite end which is closed and located towards said other leg, said lamps including means permitting immersion of the lamps into water, a plurality of electrical lead wires respectively connected to said lamps, said frame having a first portion directly connected to at least one of said legs, and a ballast incorporated in said first portion of said frame and including means connected to said lead wires for controlling all of said lamps.

2. A fluid purification device adapted to be inserted in water to be purified, the device comprising in combination, a frame including a pair of opposed legs laterally spaced from each other and adapted for insertion into the water to be purified, a plurality of water purification lamps extending between and supported by said legs, said lamps each having one end located towards one of said legs and an opposite end located towards the other leg, said lamp including means permitting immersion of the lamps into water, electrical lead wires connected to said lamps, and a ballast incorporated in said frame and including means connected to said lead wires for controlling said lamps and wherein said frame includes a cross piece extending between and directly connected to said legs and wherein said ballast is incorporated in said cross piece.

3. The device defined in claim 2 wherein all of the lead wires extend along one of said legs.

4. The device defined in claim 3 wherein one of said legs has a longitudinally extending passage receiving all of said lead wires.

5. The device defined in claim 4 wherein said one leg has a longitudinal hollow passage receiving all of said lead wires.

6. The device defined in claim 2 including a protective sleeve surrounding each said lamp.

7. A fluid purification device as defined in claim 2 wherein said ballast includes means for transmitting a voltage of on the order of 600 volts to the lamps upon initial energization of the lamps, and means for transmitting a voltage of on the order of 180 volts once the lamps have been energized.

8. A fluid purification device adapted to be used as a module with other modules to be inserted in a body of water to be purified, the device comprising in combination a frame including a pair of opposed legs laterally spaced from each other and adapted for insertion into the water to be purified, a plurality of water purification lamps extending between and supported by said legs, said lamps including means permitting immersion of the lamps into water, a plurality of electrical lead wires respectively connected to said lamps, and a ballast incorporated in a portion of said frame directly connected to at least one of said legs, said ballast including means connected to said lead wires for controlling all of said lamps.

9. The fluid purification device defined in claim 8 wherein said portion comprises a cross piece extending between said legs above an uppermost purification lamp and wherein said ballast is incorporated in said cross piece.

10. The fluid purification device defined in claim 9 wherein said electrical lead wires are located in a longitudinal passage contained in one of said legs.

11. The fluid purification device defined in claim 10 wherein said ballast including means for transmitting a voltage of on the order of 600 volts to the lamps upon initial energization of the lamps, and means for transmitting a voltage of on the order of 180 volts once the lamps have been energized.

12. The fluid purification device defined in claim 8 wherein the electrical lead wires extend along one of said legs.

13. A fluid purification device as defined in claim 8 wherein said ballast includes means for transmitting a voltage of on the order of 600 volts to the lamps upon initial energization of the lamps, and means for transmitting a voltage of on the order of 180 volts once the lamps have been energized.

14. A fluid purification device comprising in combination a frame including a pair of opposed legs laterally spaced from each other, a plurality of water purification lamps extending between and supported by said legs, a plurality of electrical lead wires respectively connected to said lamps, and a ballast incorporated in said frame and including means connected to said lead wires for controlling all of said lamps, and wherein one of said legs has a longitudinal passage receiving all of said wires while the other leg is free of any wires.

15. In combination with means containing a body of water to be purified, a water purification module located in the water and comprising in combination a frame including a plurality of water purification lamps located in the water, a ballast mounted on said frame and connected to said lamps for controlling the lamps.

16. The combination defined in claim 15 including a plurality of said modules located in the water.

* * * * *